US00PP24066P3

(12) United States Plant Patent
Nielsen

(10) Patent No.: US PP24,066 P3
(45) Date of Patent: Dec. 3, 2013

(54) *OSTEOSPERMUM* PLANT NAME 'DAOSTREOGTYVE'

(50) Latin Name: *Osteospermum ecklonis*
Varietal Denomination: DAOSTREOGTYVE

(75) Inventor: Rune Harboe Nielsen, Grönnegyden (DK)

(73) Assignee: Dalina Genetics A/S, Odense N (DK)

( * ) Notice: Subject to any disclaimer, the term of this patent is extended or adjusted under 35 U.S.C. 154(b) by 52 days.

(21) Appl. No.: 13/385,315

(22) Filed: Feb. 14, 2012

(65) Prior Publication Data

US 2013/0212762 P1 Aug. 15, 2013

(51) Int. Cl.
*A01H 5/00* (2006.01)

(52) U.S. Cl.
USPC ..... Plt./360

(58) Field of Classification Search
USPC ..... Plt./360
See application file for complete search history.

(56) References Cited

U.S. PATENT DOCUMENTS

PP23,502 P3 * 3/2013 Kristensen ..... Plt./360

OTHER PUBLICATIONS

Young Flowers "Dalina Genetics" see p. 31 'rubina' available at http://www.youngflowers.dk/PDF/GB/dalinagenetics2013.pdf accessed May 20, 2013.*
PLUTO citation for 'DAOSTREOGTYVE'.*
Printout of application information from Community Plant Variety Office (CPVO) website for corresponding CPVO application No. 2011/1945 filed Aug. 9, 2011 (1 page) (http://www.cpvoextranet.cpvo.europa.eu).
Printout of application information from Canadian Food Inspection Agency website for corresponding Canadian Plant Breeders' Rights application No. 11-7386 filed Oct. 6, 2011 (1 page) (http://www.inspection.gc.ca/plants/plant-breeders-rights/plant-varieties-journal/eng/1299170381112/1299170471284).

* cited by examiner

*Primary Examiner* — Wendy C Haas
(74) *Attorney, Agent, or Firm* — Foley & Lardner LLP

(57) ABSTRACT

A new distinct cultivar of *Osteospermum* plant named 'DAOSTREOGTYVE', characterized by being a compact cultivar, with globular upright to spreading shape; Very well branching (8-14 per plant) with stiff and strong lateral stems and small thick leaves. Color of leaves green RHS 139A (upper side) and green RHS 137B (underside); Ray florets being RHS Red 39A when opening and developing into RHS Red 53B when fully open on upper side; and disc florets that appear RHS grayed-orange 166A.

7 Drawing Sheets

Latin name of the genus and species of the claimed plant: *Osteospermum ecklonis*.

Variety denomination: 'DAOSTREOGTYVE'.

BACKGROUND OF THE INVENTION

The present invention relates to a new and distinct cultivar of *Osteospermum* plant, botanically known as *Osteospermum ecklonis* (DC) T Norl., commonly known as Cape Daisy and hereinafter referred to by the cultivar name 'DAOSTREOGTYVE'.

The new *Osteospermum* cultivar is a product of a planned breeding program conducted by the inventor, Rune Nielsen, in Stige, Denmark. The objective of the breeding program is to develop a new *Osteospermum* cultivar with good garden performance, well branching growth, continuous flowering and an attractive inflorescence color.

The new *Ostospermum* cultivar is originated from a mutation found in 'DAOSSEKSTEN' (U.S. Plant Patent Application Publication No. 20120255082) selected by the inventor in 2009, in Stige, Denmark.

Asexual reproduction of the new *Osteospermum* cultivar by terminal cuttings was first performed in November, 2009 in Stige, Denmark, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'DAOSTREOGTYVE', which in combination distinguish this *Osteospermum* as a new and distinct cultivar:

1. Compact cultivar, with globular upright to spreading shape;
2. Very well branching (8-14 per plant) with stiff and strong lateral stems and small thick leaves. Color of leaves Green RHS 139A (upper side) Green RHS 137B (underside);
3. Ray florets RHS Red 39A when opening and developing into RHS Red 53B when fully open on upper side; and
4. Disc florets that appear grayed-orange (RHS 166A).

Plants of the new *Osteospermum* 'DAOSTREOGTYVE' differ from 'DAOSSEKSTEN' (U.S. Plant Patent Application Publication No. 20120255082), from which it is mutated, in the traits described in Table 1.

TABLE 1

| Comparison with Parent Variety | | |
|---|---|---|
| Trait | New Cultivar 'DAOSTREOGTYVE' | Mutation from 'DAOSSEKSTEN' (U.S. Plant patent application Publication No. 20120255082) |
| Plant Size | | |
| Height: | About 13 cm. | About 13 cm. |
| Diameter: | About 16 cm. | About 16 cm. |
| Overall Plant Shape: | Globular upright to spreading, with very good basal and axillary branching. | Globular upright to spreading, with very good basal and axillary branching. |
| Stem | | |
| Length: | About 6 cm. | About 6 cm. |
| Diameter: | About 5 mm | About 5 mm |
| Strength: | Stiff and strong. | Stiff and strong. |
| Color: | RHS Yellow-green 144A. | RHS Yellow-green 144A. |
| Number of Inflorescence heads per Plant: | About 35. | About 35. |
| Flower Size Diameter: | About 6.5-7 cm. | About 6.5-7 cm. |
| Mature Petal Color (upper surface): | RHS Red 53B. | RHS Orange 26A. |
| Color of disc florets (as they appear when sitting in composite flower head). | RHS Grayed-orange 166A. | RHS Gray-brown N199A. |

Of the many commercial cultivars known to the present inventor, the most similar in comparison to the new *Osteospermum* 'DAOSTREOGTYVE' is the *Osteospermum* cultivar 'Cape Daisy® Terracotta', in the characteristics described in Table 2:

TABLE 2

| Comparison with Similar Variety | | |
|---|---|---|
| Trait | New Cultivar 'DAOSTREOGTYVE' | Comparison Cultivar 'Cape Daisy ® Terracotta' |
| Plant Size | | |
| Height: | About 13 cm. | About 14 cm. |
| Diameter: | About 16 cm. | About 17 cm. |
| Overall Plant Shape: | Globular upright to spreading, with very good basal and axillary branching. | Upright to spreading, with basal branching. |
| Stem | | |
| Length: | About 6 cm. | About 3 cm. |
| Diameter: | About 5 mm | About 5 mm. |
| Strength: | Stiff and strong. | Medium strong. |
| Color: | RHS Yellow-green 144A. | RHS Yellow-green 144B. |
| Number of Inflorescence heads per Plant: | About 35. | About 25. |
| Flower Size Diameter: | About 6.5-7 cm. | About 8 cm. |
| Mature Petal Color (upper surface): | RHS Grayed-orange 166A. | RHS Orange N25D |

TABLE 2-continued

| Comparison with Similar Variety | | |
|---|---|---|
| Trait | New Cultivar 'DAOSTREOGTYVE' | Comparison Cultivar 'Cape Daisy ® Terracotta' |
| Color of disc florets (as they appear when sitting in composite flower head). | RHS Grayed-orange 166A. | RHS Brown 200A |

BRIEF DESCRIPTION OF THE PHOTOGRAPHS

The accompanying photographs illustrate the overall appearance of the new *Osteospermum* 'DAOSTREOGTYVE' showing the colors as true as is reasonably possible with colored reproductions of this type. Colors in the photographs may differ slightly from the color value cited in the detailed botanical description, which accurately describe the color of 'DAOSTREOGTYVE'.

DETAILED BOTANICAL DESCRIPTION

Figure 1:
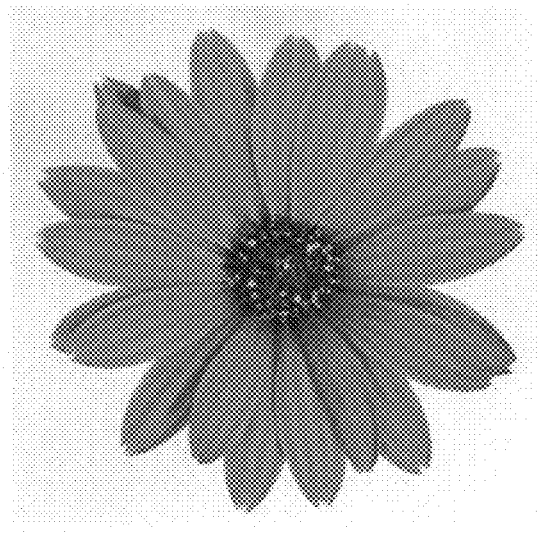
FIG. 1 shows a close-up view of the composite flower head from 'DAOSTREOGTYVE'.
Figure 2:
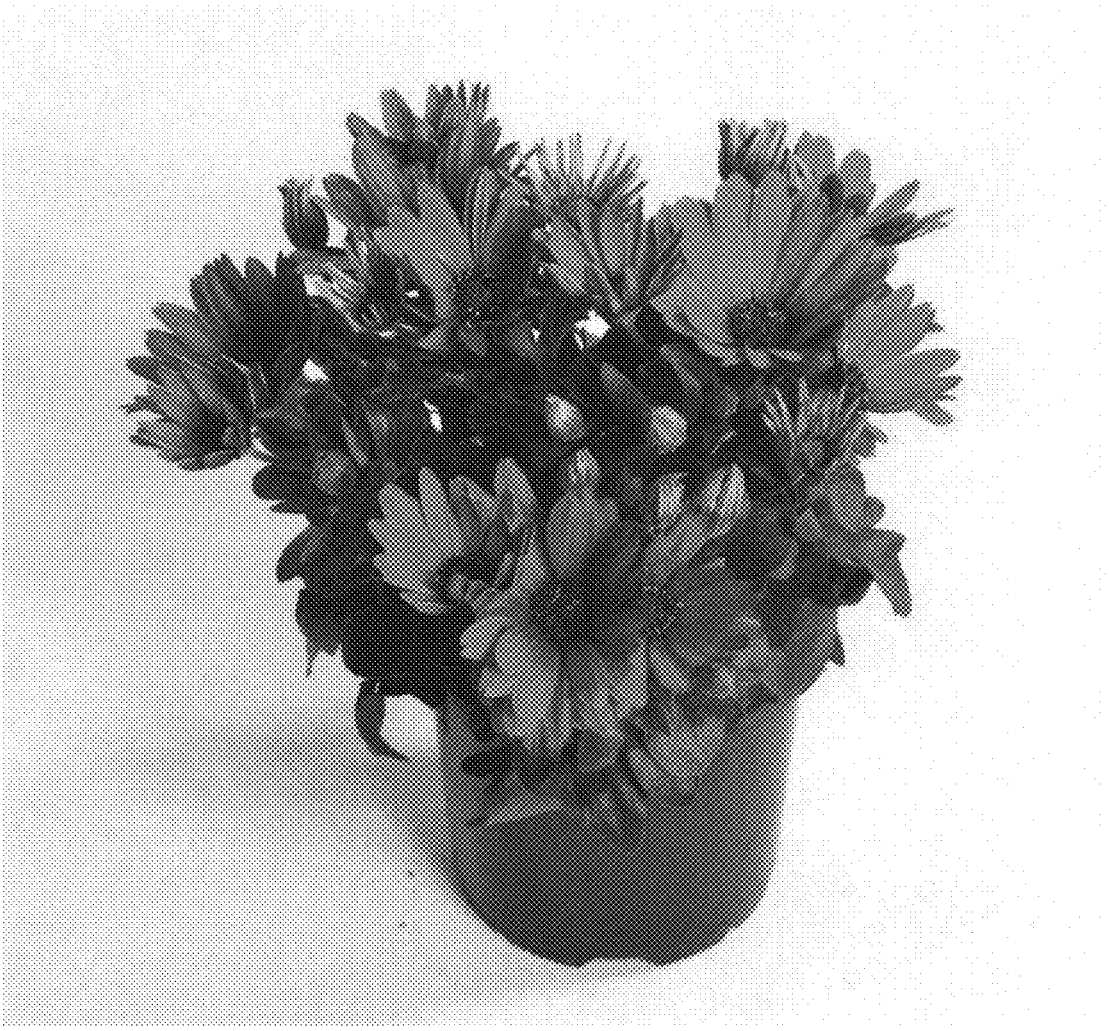
FIG. 2 shows a side view perspective of a typical flowering plant of 'DAOSTREOGTYVE' in a 11 cm pot, at 12 weeks of age after planting.
Figure 3:
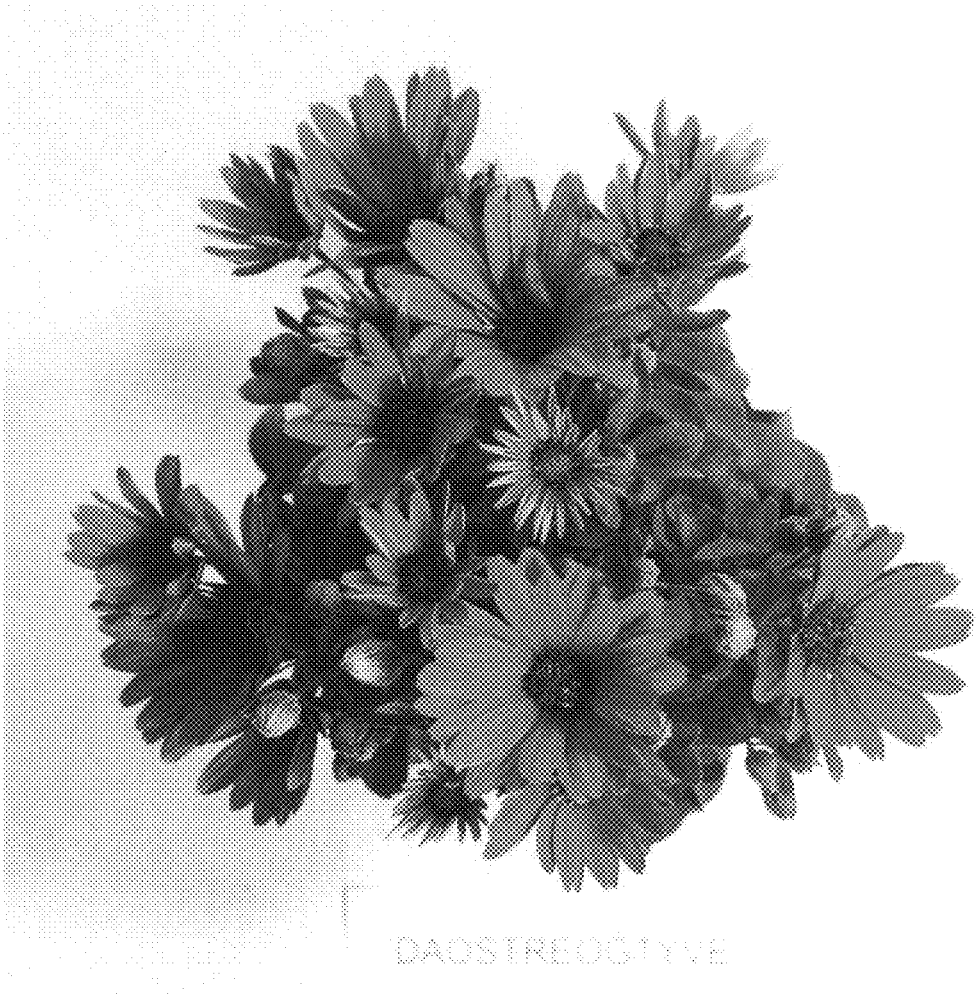
FIG. 3 shows a top-down perspective of a typical flowering plant of 'DAOSTREOGTYVE' in a 11 cm pot, at 12 weeks of age after planting.
Figure 4:
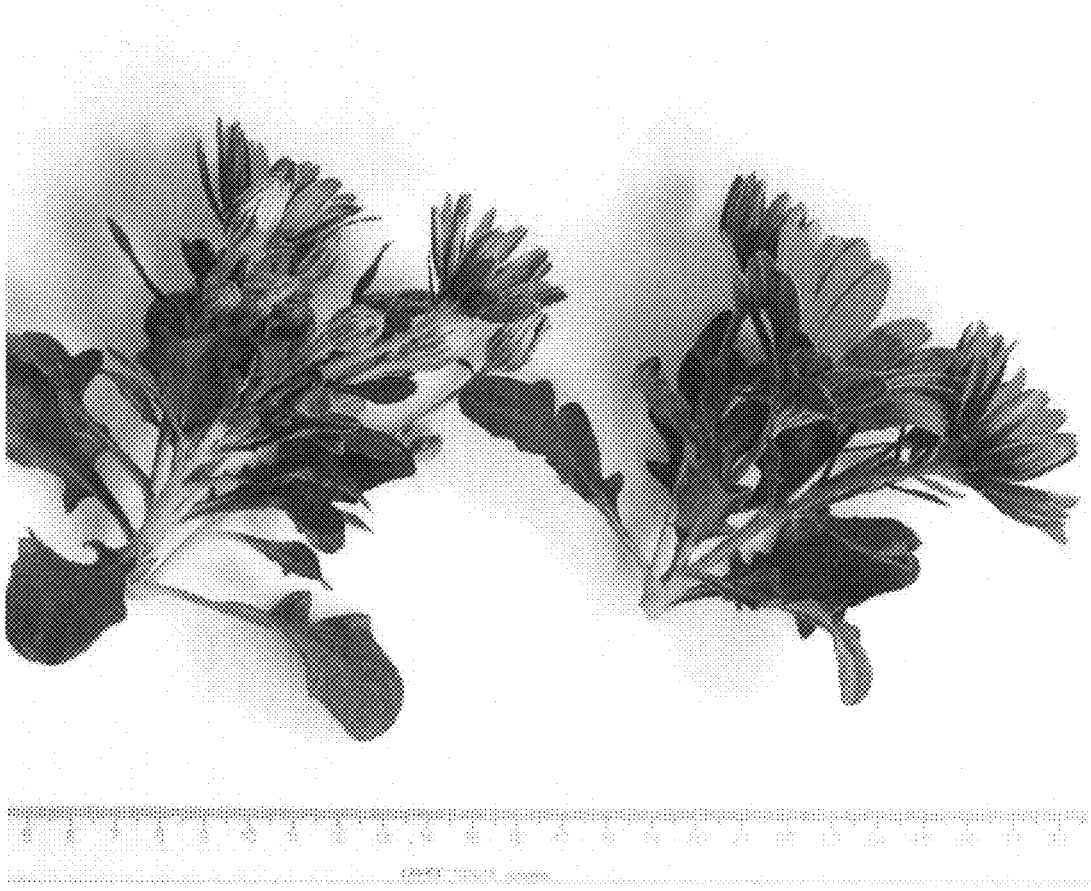
FIG. 4 shows a close-up view of the typical lateral stems with leaves and buds of 'DAOSTREOGTYVE'.
Figure 5:
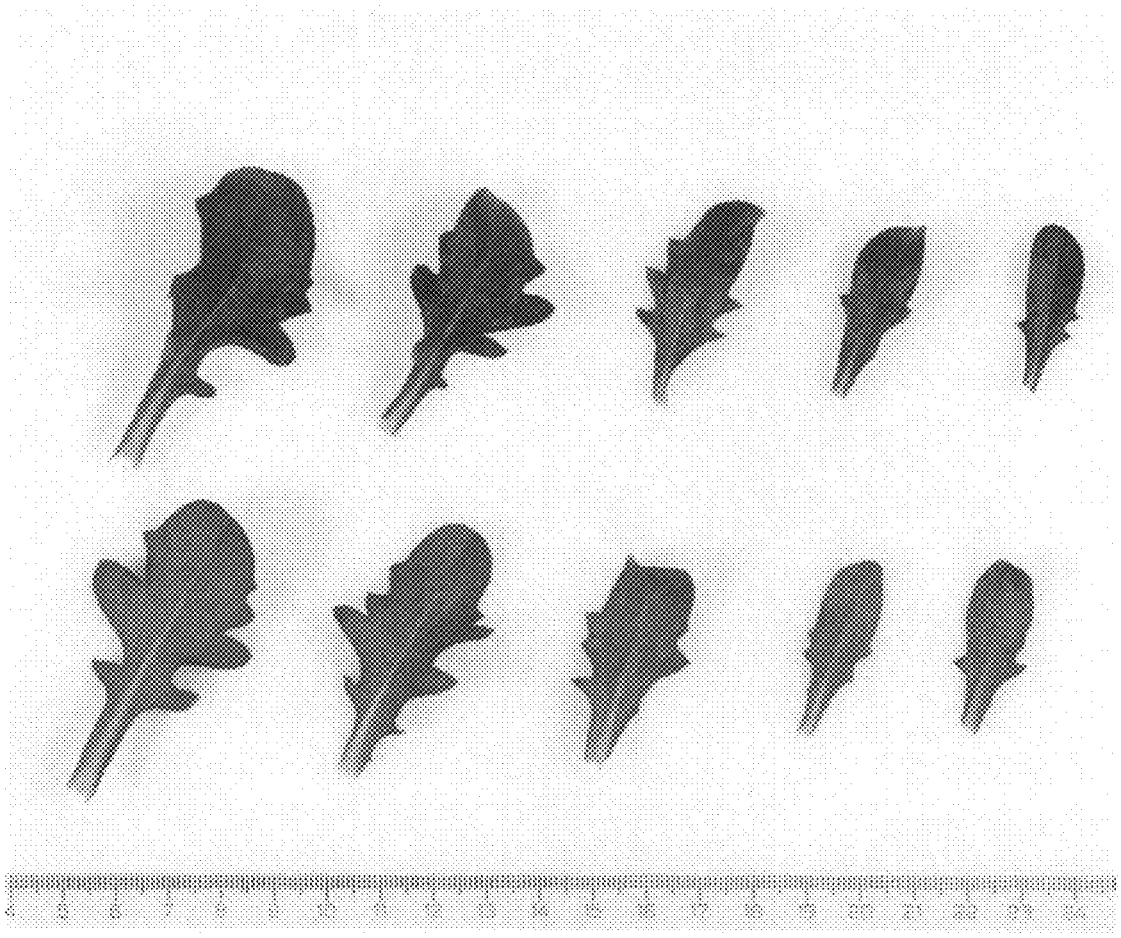
FIG. 5 shows a close-up view of the different leaf sizes of 'DAOSTREOGTYVE'.
Figure 6:
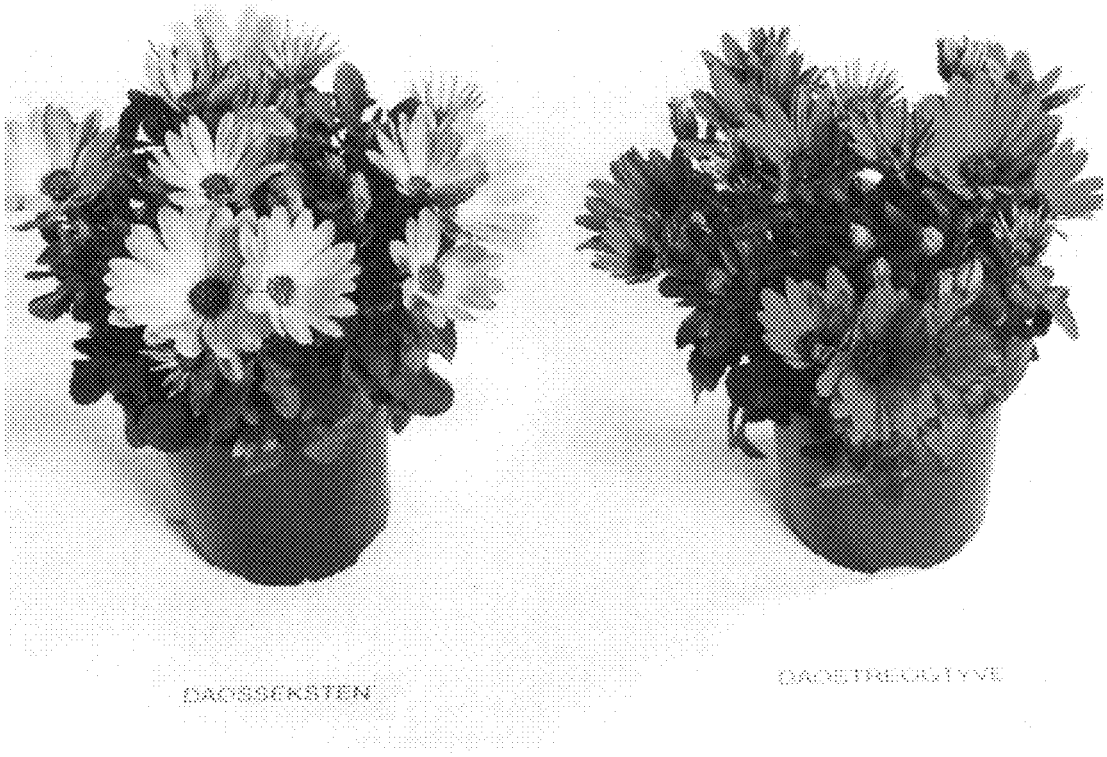
FIG. 6 shows a comparison between the cultivar 'DAOSSEKSTEN' (U.S. Plant Patent Application Publication No. 20120255082) and 'DAOSTREOGTYVE' (mutation from 'DAOSSEKSTEN')
Figure 7:
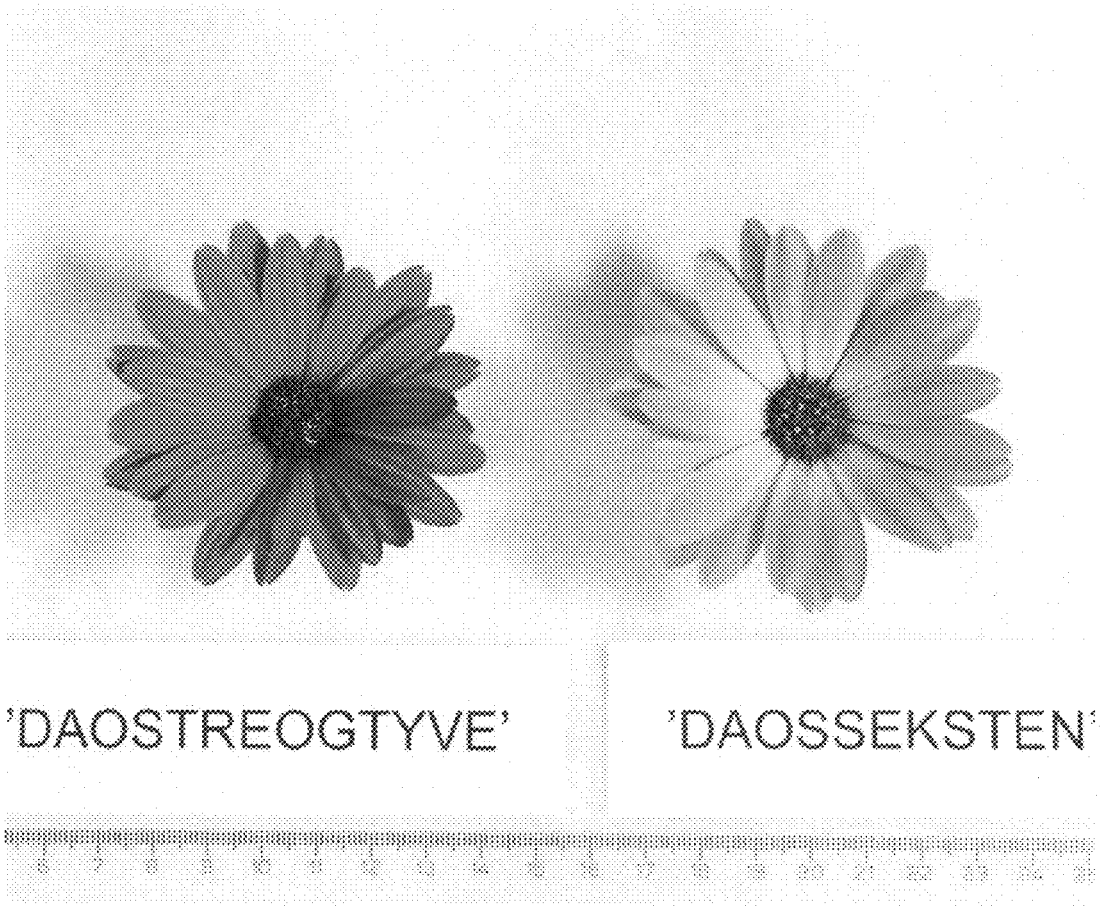
FIG. 7 shows a comparison between 'DAOSSEKSTEN' and 'DAOSTREOGTYVE'.

The new *Osteospermum* 'DAOSTREOGTYVE' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Osteospermum* 'DAOSTREOGTYVE' as grown in a glasshouse, equipped with heat, assimilation light and ebb/flood watering system in Odense, Denmark, under conditions which closely approximate those generally used in commercial practice. The plants were grown in 14° C., with a venting temperature on 16° C. Assimilation light was given when natural daylight was below 3000 lux and the day length was extended to 16 hours. The EC levels in the soil were kept at about 2.5-3.5 and pH around 6.0 during the production. Plant growth was regulated 3 times during the production period, using 3% CYCOCEL (chlormequat-chloride) as a drench (80-100 ml/pot).

Color references are made to The Royal Horticultural Society Colour Chart (R.H.S.), Colour Chart 2001 edition, Color values were taken under January daylight conditions at approximately 11:00-13:00 in Stige, Denmark. The age of the 'DAOSTREOGTYVE' plants described is 12 weeks from potting.

Classification:

*Botanical.*—*Osteospermum ecklonis* (DC) Norl.

Mutation from: 'DAOSSEKSTEN' (U.S. Plant Patent Application Publication No. 20120255082).

Propagation:

*Type*.—Vegetative terminate cuttings.

*Time and temperature to initiate roots*.—About 9 to 13 days at 19 to 21° C. in tunnels in a greenhouse.

*Time and temperature to produce a rooted young plant*.—About 4 to 5 weeks at 18° (initiation period benefits from 19 to 21° C.).

*Rooting habit*.—Vigorous, white to grayed yellow and well branched.

Plant description:

*General appearance and form*.—Globular upright, with basal branching. Inflorescences in composite heads. Freely branching with lateral flowering branches forming at every node.

*Growth rate*.—Growing about 1 cm per week during production period.

*Plant height*.—About 12 cm to 15 cm.

*Plant width* (*spread*).—About 15 cm to 17 cm.

*Crop time to produce a mature flowering plant*.—It requires 4 to 5 weeks to produce a young plant in a 35 mm propagation plug. After potting 12 to 14 weeks are required to produce finished flowering plants in 11 cm pots.

Stem:

*Shape*.—Round.

*Length*.—About 4 cm to 6 cm.

*Diameter*.—About 3 mm to 5 mm.

*Strength*.—Stiff and strong.

*Aspect*.—Upright.

*Texture*.—Smooth and glabrous.

*Color*.—Mature: RHS Yellow-green 144A. Immature: RHS Yellow-green 144C.

Branches:

*Branching habit*.—Basal branching with very good lateral branching.

*Number of branches per plant*.—About 3 to 5 branches, spreading into 18 to 20 lateral branches.

*Length* (*including flowers*).—About 11 cm to 12 cm.

*Diameter*.—About 5 mm.

*Strength*.—Stiff and strong.

*Apect*.—Upright to spreading.

*Texture*.—Smooth and glabrous.

*Color*.—Mature: RHS Yellow-green 144A. Immature: RHS Yellow-green 144C.

*Internode length*.—About 4 to 10 mm.

*Internode color*.—RHS Yellow-green 144A.

Foliage description:

*Arrangement*.—Alternate.

*Number of leaves per branch*.—About 8 to 12 per branch.

*Length*.—About 4 cm to 7 cm.

*Width*.—About 1 cm to 3 cm.

*Overall shape of leaf*.—Obovate to spatulate with 1 to 3 acuminate teeth on each side.

*Shape at apex*.—Obtuse.

*Shape at base*.—Attenuate.

*Margin*.—Dentate (1 to 3 lobes on each leaf).

*Texture*.—Upper surface: Pubescent with scattered short, stiff hairs. More hairs on the edges of leaf. Lower surface: Pubescent with scattered short, stiff hairs More hairs along veins and on the edges of leaf. Young leaves appear more hairy than older.

*Color of developing foliage*.—Upper surface: RHS Green 137A. Lower surface: RHS Green 137C.

*Color of mature foliage*.—Upper surface: RHS Green 139A. Lower surface: RHS Green 137B.

*Venation pattern*.—Trinerved with veins along nerves.

*Venation color*.—Upper surface: RHS Yellow-green 147B. Lower surface: RHS Yellow-green 146B.

Inflorescence description:

*Arrangement and shape*.—Tubular disc floret and flat, lanceolate ray florets in composite flower heads, developed from terminal and axillary shoots. The peduncles lift the Inflorescences 0-4 cm above the foliage. Inflorescences face upright to 70° angle from vertical.

*Natural flowering season*.—*Osteospermum* is a bedding plant, with a flowering season from early spring to late autumn. Temperatures below 20° C. will increase flowering, temperatures above 20° C. will reduce flowering.

*Time to flower*.—65 to 85 days.

*Inflorescence longevity on the plant*.—Inflorescence will maintain good color and substance for about 5-10 days; however, the longevity of individual inflorescence is highly dependent on temperature and light conditions. Inflorescence persistent.

*Quantity of inflorescences heads*.—Freely flowering; about 30 to 40 buds and open inflorescences per plant.

*Fragrance*.—Very discreet smell.

*Bud* (*inflorescences head*).—Rate of opening (from showing 1 to 5 days. The rate of opening is highly color to fully open flower): dependent on temperature and light conditions. Length: About 12 mm. Diameter: About 10 mm. Shape: Acuminate. Texture: Pubescent with small hairs. Color: RHS Yellow-green 144A at base to RHS Green 137A at apex.

*Peduncle*.—From both terminate and axillary shoots. Length: About 3 to 5 cm. Diameter: About 2 mm. Angle: About 0 to 30° from vertical. Strength: Medium strong. Texture: Pubescent with small white hairs. Color: RHS Yellow-green 144A.

*Inflorescence head*.—Length: About 10 mm. Diameter: About 7 to 8 cm.

*Ray florets*.—Quantity per Inflorescence head: 20 to 24. Length: 30 mm. Widths: 7 to 9 mm. Overall shape: Spatulate. Shape at apex: Obtuse. Shape at base: Acute. Margin: Entire, small cleft at apex. Texture: Upper surface: smooth, matte, slightly furrowed. Lower surface: smooth, matte, slightly furrowed. Color upper side: When opening RHS Red 39A developing into RHS Red 53B when fully open. Color underside: Stripes of various colors; RHS Grayed-red 182A, RHS Grayed-orange 174B and RHS Grayed-purple 187A.

*Disc florets*.—Quantity per Inflorescence head: 65 to 75. Length: 6 mm. Diameter: 1 mm. Color Tip: RHS Grayed-purple 187A. Middle: RHS Gray-brown N199A. Lower half: White with very small stains of RHS Red-purple 58C gives this part a light purple look.

*Phyllary.*—15 to 20. Length: 8 to 10 mm. Width: 1 to 2 mm. Overall shape: Lanceolate. Apix: Narrow Acuminate. Base: Fused. Margin: Entire. Color: RHS Green 137A.

Reproductive organs:

*Androecium.*—Location: Disc florets only. Stamen number: 5 fused. Stamen length: About 5 mm. Anther shape: Linear, fused. Anther length: About 2 mm. Pollen amount: Medium amount. Pollen color: RHS Yellow-orange 14A.

*Gynoecium.*—Location: Ray and disc florets. Quantity: 1. Pistil length: About 5 mm. Stigma shape: Brush-like, cleft 1.5 mm deep. Stigma length: About 2 mm. Stigma color: RHS Grayed-purple N186A. Style length: About 4 mm. Style color: Lower part: RHS White N155A. Upper part: RHS Red-purple 70A. Ovary color: RHS Yellow-green 145B.

Seed/fruit: Seed and fruit production has not been observed.

Disease/pest resistance: Resistance to pathogens and pests common to *Osteospermum* has not been observed.

Disease/pest susceptibility: Susceptibility to pathogens and pests common to *Osteospermum* has not been observed.

Temperature tolerance: Plants of the new *Osteospermum* have exhibited good tolerance to rain, wind and drought; however, flowering may cease during hot periods (temperatures above 25° C.). Low temperature tolerance to 1° C.

What is claimed is:

1. A new and distinct cultivar of *Osteospermum* plant named 'DAOSTREOGTYVE', as illustrated and described herein.

* * * * *